United States Patent [19]

Joh et al.

[11] Patent Number: 4,707,315
[45] Date of Patent: Nov. 17, 1987

[54] METHOD OF MAKING A BLOOD PUMP

[75] Inventors: Yasushi Joh, Yokohama; Toshio Nagase, Tsukuba, both of Japan

[73] Assignee: Nippon Zeon Co., Ltd., Tokyo, Japan

[21] Appl. No.: 734,367

[22] Filed: May 15, 1985

[30] Foreign Application Priority Data

May 18, 1984 [JP] Japan .................... 59-99825

[51] Int. Cl.$^4$ ............................................. B29C 41/18
[52] U.S. Cl. ........................... 264/129; 264/259; 264/302; 264/303; 264/DIG. 60; 623/3
[58] Field of Search ....... 264/259, 302, 303, DIG. 60, 264/129; 249/111; 425/809, 813; 623/3

[56] References Cited

U.S. PATENT DOCUMENTS 2,830,325  4/1958  Bray ...................................... 249/111

OTHER PUBLICATIONS

E. B. Greenspun, "Slush Molding Vinyl Plastisols", Modern Plastics, Oct. 1950, pp. 102–104.

Primary Examiner—Jeffery Thurlow
Assistant Examiner—Leo B. Tentoni
Attorney, Agent, or Firm—Armstrong, Nikaido, Marmelstein & Kubovcik

[57] ABSTRACT

In a slush molding method of making a blood pump for an artificial heart, a heat insulating material is applied to at least a portion of the outer surface of a mold in which the blood chamber formed so that at least a part of the blood chamber is thinned in a tapered form.

13 Claims, 20 Drawing Figures

FIG. 5 (A) PRIOR ART 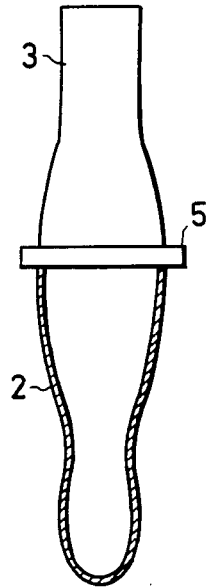
FIG. 5 (B) PRIOR ART 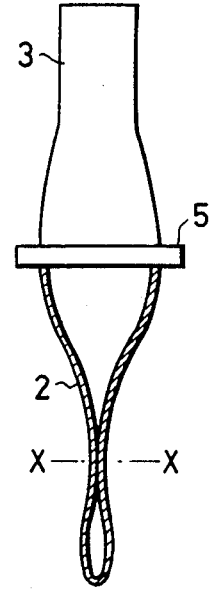
FIG. 5 (C) PRIOR ART 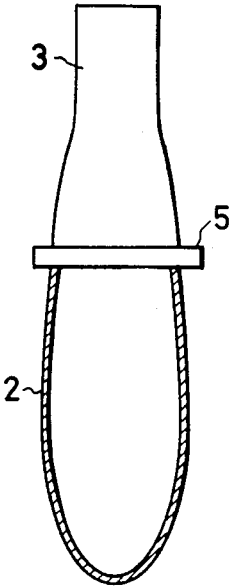
FIG. 6 PRIOR ART
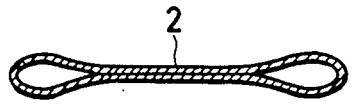

FIG. 7 PRIOR ART
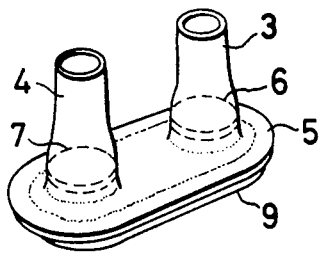
FIG. 8 PRIOR ART (A)
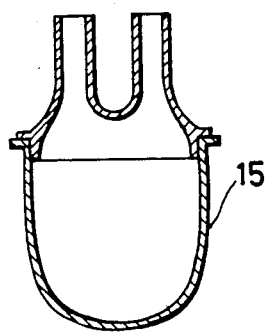
FIG. 8 PRIOR ART (B)
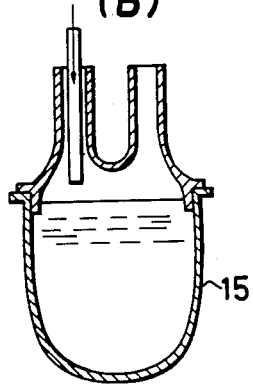
FIG. 8 PRIOR ART (C)
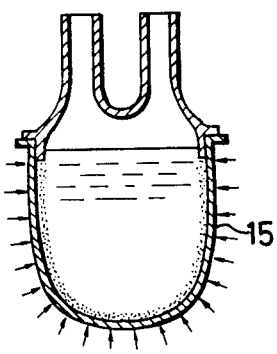
FIG. 8 PRIOR ART (D)
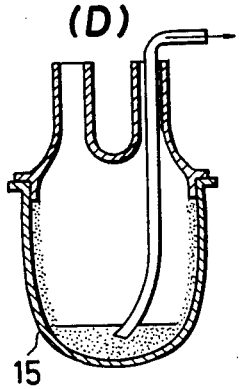
FIG. 8 PRIOR ART (E)
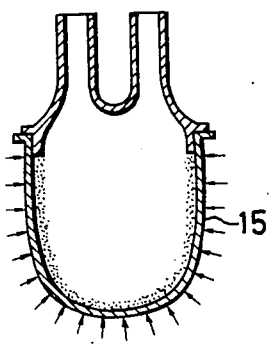
FIG. 8 PRIOR ART (F)
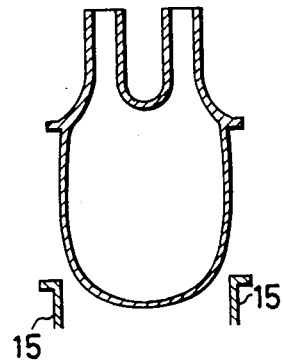

METHOD OF MAKING A BLOOD PUMP

BACKGROUND OF THE INVENTION

1. Field of the Invention

This invention relates to a method of making a sac-type blood pump for use in an artificial heart.

2. Description of the Prior Art

In recent years, work has been done on the development of an "artificial heart" i.e. a blood pump to be used outside of the body of a patient to provide cardiac assistance temporarily in place of his natural heart during, for example, heart surgery. For clinical applications of the artificial heart, a particular problem encountered is the formation of thrombi in the artificial heart. The prevention of thromboses is regarded as a problem which is extremely difficult to solve. The prevention of thromboses is influenced by factors such as the constituent material and the design of the blood pump, particularly the smoothness of the inner surface, the dynamic behavior when being driven, the blood flow pattern and other factors. These factors are related in a complex manner.

FIGS. 1 through 4 give schematically various views of a known sac-type blood pump and its blood chamber. FIGS. 5 and 6 show the course of deformation of the blood chamber depending on the rise and fall of fluid pressure.

The sac-type blood pump consists of a pressure-proof housing or outer case 1 made of such materials as polycarbonate or polyurethane and a flat sac-shaped blood chamber 2 fluid-tightly held in the outer housing 1. On a top portion or cover attached to this blood chamber 2, there are provided an inlet conduit 3 and an outlet conduit 4, protruding upwardly and substantially parallel to each other. The conduits 3 and 4 communicate with the blood chamber 2. The top cover is also provided, on the circumference, with flange 5 for fluid-tightly holding it in the outer housing 1. The inlet and outlet conduits 3 and 4 each have a check valve (not shown) mounted therein and adapted to prevent reverse flow so that the blood is introduced through the inlet conduit 3 into the blood chamber 2 and intermittently pumped out through the outlet conduit 4.

The intermittent pumping out of blood is caused by alternately introducing and discharging of a pressure medium or fluid through a port 8 at the lower end of the housing 1 with concomitant repeated expansion and contraction of the blood chamber.

The inventors have studied the thrombosis problem in animal experiments and have determined that there is a tendency of thrombuses to form at regular places. Specifically, formation of a thrombus is rarely found around the inlet and outlet conduits 3 and 4 but often observed near the bottom of the blood chamber 2, in particular at the narrow sides close to the bottom.

Further, the inventors have observed the probability of thrombus formation to be low where blood flows at relatively high flow rate and to be more frequently in stagnant portions in the blood-stream. In other words, thrombi are rarely formed near the conduits where rheologically blood flows relatively fast while a tendency towards stagnation in the blood-stream, found in the vicinity of the bottom of the blood chamber 2, appears to induce thrombosis.

The conventional blood chamber 2 has a substantially uniform thickness over the whole, as shown in FIGS. 3 and 4. When the blood chamber 2 received in the housing 1 (as diagrammed in FIG. 1) is pneumatically or hydraulically compressed, it is subjected to a deformation with concomitant change in volume from the state shown in FIG. 5A to the state shown in FIG. 5B.

FIG. 5A shows a deformation of the blood chamber 2 caused by positive pressure into the housing 1 from the shape under the unloaded condition as diagrammed in FIG. 3. As understood from these, the deformation of the blood chamber 2 is not uniform in respect to the cross section of the chamber but compression occurs initially, or primarily, in the vicinity of the center of the area defined by the opposite wider sides. As the compression advances, deformation spreads over the surrounding portions. Meanwhile a partial contact of the wider sides with each other occurs at the most easily deformable center, as illustrated in FIG. 5B. Then the contact point spreads out left- and rightwardly and up- and downwardly. Through the influence of the progress of deformation, blood in the upper portion of the blood chamber 2 flows directly to the outlet conduit 4 while blood in the lower portion is forced to flow about along the inner surface of the sides, resulting in a tendency towards stagnation of the blood stream there. An additional disadvantage is that total compression of the blood chamber 2 cannot be attained for instance, pneumatically, owing to the resistance of its elastic wall. Thus parts of the wall of the blood chamber 2 remain uncontacted near the bottom and at the narrower sides, as seen in FIGS. 5B and 6, where blood flow is stagnant, compared with the center zone, where the opposite wider sides, become flattened until they have been placed in complete contact with each other. In those portions of stagnant blood flow, poor exchange occurs with new blood introduced during each expansion of the blood chamber 2 (FIG. 5C) caused by the reduction of pressure in the housing 1 is found.

In the animal experiments, the formation of thrombi was often observed in the area indicated by cross-hatching in FIGS. 2.

In view of these, it is essential for preventing the formation of thrombi to compress the blood chamber 2 so that it is flattened as completely as possible and thus substantially no portions remain uncontacted.

The inventors made further observation that the pattern of compression, for example, by pneumatic means, is preferable which consists of deformation accompanied by reduction in volume beginning near the above-defined center, followed by deformation in the vicinity of the bottom, and the spreading out of the deformation from there to the surroundings.

Out of various methods or constructions conceivable for permitting above-mentioned compression pattern, it is the most effective that compared with the conventional blood chamber having substantially uniform thickness over the whole, the basic shape of the blood chamber 2 is unchanged, but the surrounding wall is not uniform and varies from place to place in thickness.

SUMMARY OF THE INVENTION

Accordingly, it is an object of the present invention to provide a method of making a blood pump which operates in particular without forming thrombi in the blood chamber and thus has sufficient durability guaranteed.

It is another object of the present invention to provide a method of making a blood pump permitting minimized stagnation of the blood-stream in the vicinity of the bottom of the blood chamber.

It is still another object of the present invention to provide a method of making a blood pump comprising a blood chamber surrounded with a wall having nonuniform thickness and thus giving improved deformation pattern of the blood chamber during compression.

It is still another object of the present invention to provide a modified slush molding method of making a blood pump comprising a blood chamber surrounded with a wall having at least a part thereof thinned in tapered form.

These and other objects have been attained by a method of making a blood pump comprising steps of forming a cover which has an inlet conduit portion for introducing blood and an outlet conduit portion for pumping out the blood, putting the cover onto a cuplike mold in liquid-tight manner, covering at least a part of the outer surface of the mold with a heat insulating material, pouring a plastisol of polyvinyl chloride into the mold to the level that the plastisol comes into contact with the cover, and heating the mold from the exterior so that the plastisol is gelled to form a blood chamber.

Other and further objects, features and advantages of the invention will appear more fully from the following description.

BRIEF DESCRIPTION OF THE DRAWINGS

FIGS. 5A through 5C are side views of the cover and blood chamber part, illustrating deformation patterns of the blood chamber including contraction and expansion;

FIG. 6 is a cross-sectional view taken along line X—X of FIG. 5B;

FIG. 7 is a perspective view of the cover;

FIGS. 8A through 8F are cross-sectional views illustrating the process of molding the blood chamber.

DETAILED DESCRIPTION OF THE INVENTION

Figure 1:
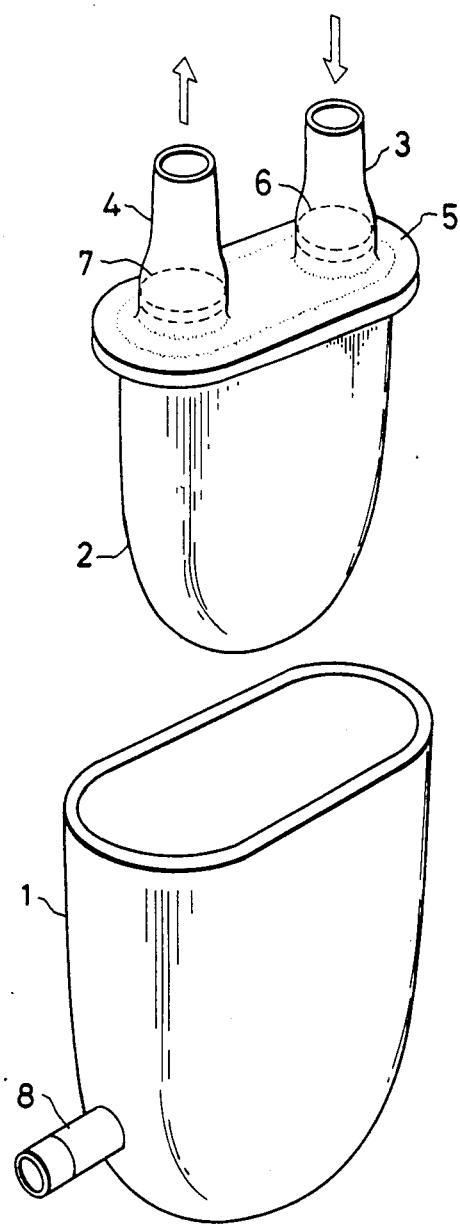
FIG. 1 is a perspective view of two separated parts of a prior art sac-type blood pump.

The invention is concerned with an improved method of making of a blood pump by the utilization of a modified slush molding technique with a plastisol consisting of a plasticizer and polyvinyl chloride, the so-called polyvinyl chloride paste. The method according to the invention enables molding a blood chamber having any desired tapered thickness.

Polyvinyl chloride paste suitable for use in the invention is an uniform-dispersion sol of an appropriate viscosity obtained by uniformly dispersing superfine particles of polyvinyl chloride having particle sizes of less than 1 $\mu$m in a plasticizer such as dioctyl phthalate (DOP). The particle size of the resin for the polyvinyl chloride paste is very small compared with that of the usually used polyvinyl chloride, typically more than 100 $\mu$m. The characteristic of polyvinyl chloride paste resides in enabling the processing of the solution state of soft polyvinyl chloride, in particular without using any solvent. Thus, the present invention relates to an improved method of making a blood pump of polyvinyl chloride by the utilization of a modified slush molding technique. The processing of polyvinyl chloride paste is based on the application of the principle that when a metal or plastic mold having a certain heat capacity is brought into contact with polyvinyl chloride paste, the plasticizer infiltrates into particles of polyvinyl chloride in the sol and then the sol is plasticized by conduction of heat through the contact surface. As a result, a semigel film is formed on the surface of the mold. In this condition, the excess paste is removed. Then a gelled film of soft polyvinyl chloride, having an uniform thickness can be formed on the surface of the mold. Subsequently, curing is made to obtain homogenous resin film. In this case, the thickness of the film is dependent mainly on the viscosity of paste sol, heat capacity of metal mold, and period of contact between metal mold and polyvinyl chloride sol. In this way, setting desired thickness of film is easily possible by taking these conditions of molding into consideration.

The slush molding which is the basis of the method according to the invention will be described hereunder with reference to FIGS. 7 and 8.

In the first step, the cover part of the blood pump (FIG. 7) is made by the known dipping technique, as disclosed, for example, in Japanese Pat. Laid-open No. 999763/1982. There may be provided an annular projection for use in mounting a valve to the conduit 3 or 4 on the cover body. A conduit element equipped with a valve may be connected to the cover body. At any rate, the cover is provided with inlet and outlet conduits 3 and 4 for the blood. The cover has on the inner side, an annular portion 9 formed integrally. The cover part is attached to a previously-prepared metal mold 15 for molding, with the annular portion 9 just fitted in the mold, as shown in FIG. 8A. Then the mold 15 is secured fluid-tight to the cover 5. Subsequently, polyvinyl chloride plastisol such as ZEON 131A (Nippon Zeon Co., Ltd.) is poured into the molding 15, in the manner as shown in FIG. 8B, to the level indicated by the solid line. The cover-mold unit is dipped and heated in a bath at temperatures between 80° and 180° C., preferably between 90° and 140° C. When as a plastisol, a copolymer having a low softening point, such as vinyl chloride-vinyl acetate copolymer or vinyl chloride-vinyl ether copolymer instead of a homopolymer of vinyl chloride is used, relatively low temperature may be applied. Treatment should be continued preferably for several to about 30 minutes. Insufficient heating, and too short a time of treatment, results in too thin a gelled layer, while too high a temperature, and too long a time of treatment produces a too thick, and so undesired, gelled layer. Plastisol portion which has been in contact with the metal mold is gelled, and the gel layer of a uniform thickness is formed on the mold, as shown in FIG. 8C. Plastisol which is present also in the inside of the annular portion 9 formed integrally with the cover will not be gelled by virtue of the insulating property of the cylindrical portion. Thus, when the paste is being discharged in the way FIG. 8D indicates, such plastisol flows down of itself or under gravity, and this enables one to obtain a blood chamber with the so-called seamless inner surface finished so as to be free of steps. Then heat curing is carried out as shown in FIG. 8E, at temperatures within the range of preferably from 160°–240°

C., and still preferably 190°–210° C. Poor curing results at temperatures lower than 160° C. and there is the possibility of heat decomposition of polymer at not less than 240° C.

After cooling, the mold is removed. In this way, a satisfactory seamless unit of the cover and blood chamber integrated in a body, as seen in FIG. 8F, is obtained.

The method of the invention, which the inventors called partial thermal insulation method, is a modification of the slush molding technique comprising gelling a paste sol by heating to form a layer of gelled paste having a continuous thinning thickness on the portion covered with a suitable heat insulating material by means of applying the insulating material to the outer side of the mold or the side of heat medium to prevent to some extent heat conduction.

Figure 9:
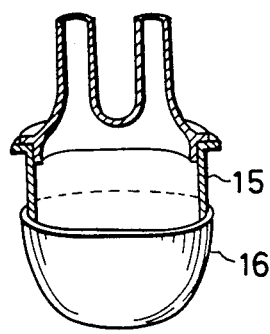
FIGS. 9 through 13 are elevational and partially sectional views of various embodiments of the method according to the invention, a heat insulating member being applied to the outer surface of the mold, and showing the cover and mold in sectional view and the whole of the insulating material.
Figure 10:
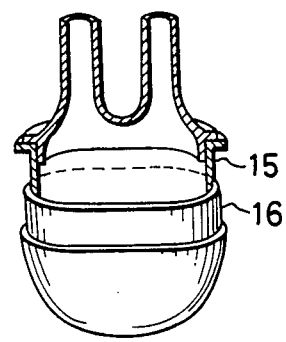

The invention will be described more fully by way of examples with reference to the accompanying drawings hereinafter:

FIG. 9 shows the first embodiment, in which a heat insulating member 16 is applied to the lower half portion of a metal mold. The mold is filled with a paste sol, and dipped into a heat bath. The heat insulating member prevents heat conduction to the portion covered with it, resulting in little heat conduction to the paste sol distant from the mold wall, and in turn, in a small thickness of semigel film to be deposited onto the inner surface of the mold. Since the mold itself is originally made of a good heat conductor the portion of the mold near the upper end portion of the high insulating member is placed in contact directly with heat medium and so receives an adequate heat, thus without production of a step in the thickness in the boundary with the heat insulating member. Change in the degree of tapering of the wall thickness, if desired, is possible by displacement with another heat insulating member of correspondent thickness or having correspondingly higher insulating property. FIG. 10 shows the second embodiment, in which a blood chamber with double-tapered zone, in particular, the thinnest area around the bottom, is desired. In this case, the mold is covered with an insulating member in the lower half area and double-covered near the bottom. It is a matter of course that multiple, such as triple or quadruple covering may be applied for obtaining desired thickness.

Figure 11:
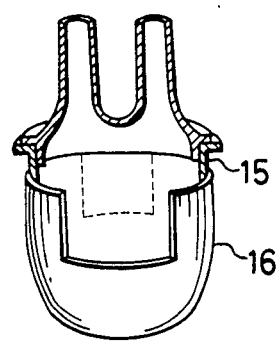
Figure 12:
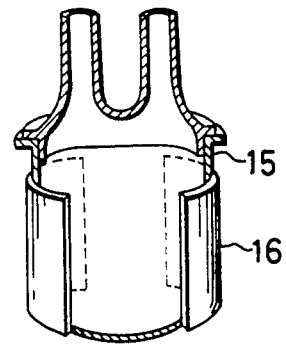
Figure 13:
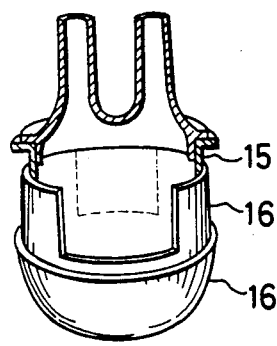

The third embodiment is shown in FIG. 11, which is the example where both the narrower sides and bottom are desired to be molded to smaller thickness, and therefore a heat insulating member is disposed near the narrower sides and bottom of the mold. FIG. 12 gives the fourth embodiment which is an example where only the narrower sides are desired to be molded to the smaller thickness. FIG. 13 is the fifth embodiment wherein both the narrower sides and the bottom of the mold are thinner, and in particular the latter is thinner than the former.

The above-described five embodiments are not limitative but it is essential to mold by arranging heat insulating member or members on the portion to be desired to be molded to a smaller thickness.

It is important for the molding according to the invention to place the insulating member as closely or fluid-tightly on the mold as possible because insufficient fluid-tightness allows the heat medium to infiltrate between the heat insulating member and the mold, resulting in unsatisfactorily taking away the effects of the invention.

As heat insulating material suitable for use in the present invention, any material having heat insulating property and heat-resistant to the slush molding temperature can be used. Typical examples are various synthetic high molecular weight polymers, in particular, the so-called engineering resins such as polyvinyl chloride, polyvinylidene chloride, polyethylene terephthalate, nylon 6, nylon 66; and polycarbonate; polysulfone, acryl resins; polyacetal resin; ABS resin; hard rubbers such as ebonite; polyurethane, and epoxy resin. Additionally, calcined carbon, ceramics and other inorganic insulating materials; natural wood; asbestos; and cement can be used.

The member made from any of the above-mentioned heat insulating materials may be integrally formed with the metal mold, and preferably is detachable from the mold and thus freely replaceable with any other member made from different insulating material.

Further, the thickness of blood chamber to be molded, which is dependent on the amount of plasticizer for P.V.C., is usually 1 to 3 mm. The thickness of the thin portion formed by the molding method according to the invention however is preferable 0.3 to 1 mm. Less thickness than 0.3 mm is associated with poor strength, and greater thickness than 1 mm of the portion does not allow it to be deformed prior to the others, thereby being against the object of the invention.

According to the invention, the cover is molded separately, and so the amount of a plasticizer to be used for molding the cover is preferably smaller than that for molding the blood chamber. Accordingly, the cover is preferably molded with polyvinyl chloride plastisol having a relatively poor content of the plasticizer, the formulation of it being, for example, polyvinyl chloride, 100 parts; dioctyl phthalate as a plasticizer, 40 to 60 parts; and organic calcium-zinc complex as a stabilizer, 3 parts.

On the other hand, the blood chamber can be deformed with concomitant change in volume, by the pneumatic drive, and thereby performs a pump function, and hence is required to be soft and elastic. Preferable composition of a suitable plastisol is an polyvinyl chloride 100 parts and dioctyl phthalate 60 to 90 parts.

Besides, the cover made from hard polyvinyl chloride to which no plasticizer is added can be used. The cover and the blood chamber are made from adhesive high molecular material are suitable to be used in the invention. Examples of this are polyurethane, epoxy resin, and polymethyl methacrylate resin. The cover made from any of these high molecular materials is capable of being subjected to fusing-adhesion to the blood chamber made from soft polyvinyl chloride by the method according to the invention.

In the preferred embodiment, the inside of the integrally molded blood chamber may be coated with a known antithrombotic material such as polyurethane-dimethylsiloxane block copolymer for the improvement in antithromboic characteristic of the surface to be brought in contact with the blood.

Figure 2:
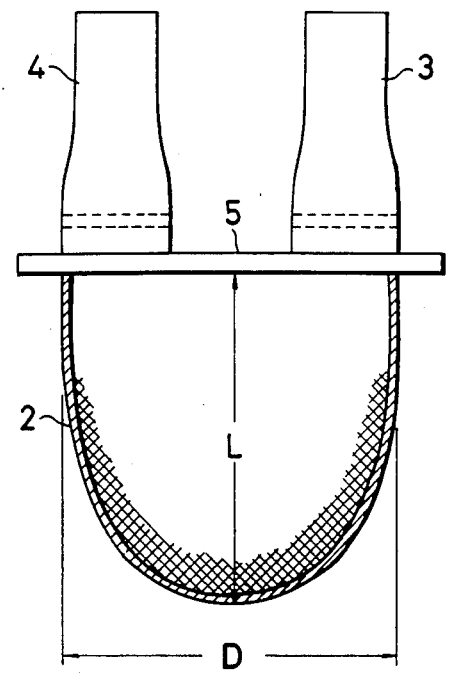
FIG. 2 is an elevational view in section of the cover and blood chamber part of the same blood pump, which is in unloaded state.
Figure 3:
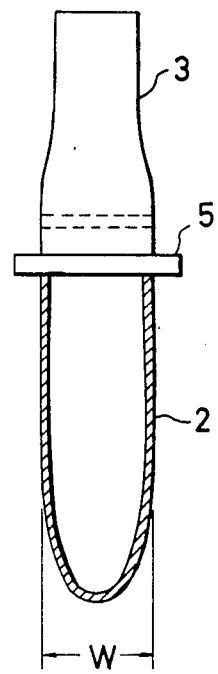
FIG. 3 is a side view of the same part.
Figure 4:
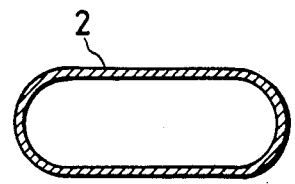
FIG. 4 is a cross-sectional view of the blood chamber.

The shape of the blood chamber of the blood pump according to the invention may be flat, as shown in FIG. 2. The ratio D/W of the largest width D of the broader side to the largest width W of the narrower side in unloaded state is within the range of 1.5 to 3.0, preferably 1.6 to 2.5, still preferably 1.8 to 2.3.

In the preferred embodiment, the ratio between the overall height L of the blood chamber 2 along the central line of it and the largest width D may be within the range:

$$0.8 \leq D/L \leq 2.0.$$

The blood chamber fulfilling these requirements can give a regular beat pattern of flattening motion per each beat caused by the pneumatic drive.

EXAMPLES

Examples 1 through 3 and Comparative Example

A cover illustrated in FIG. 7 was made from polyvinyl chloride containing DOP 70 parts by weight (to polyvinyl chloride 100 parts by weight), and then fluid-tightly mounted on a metal mold with the cylindrical portion fitted in the opening of the mold, as shown in FIG. 8. In Example 1, a heat insulating member of 15 mm in thickness made from soft polyvinyl chloride was closely attached to the lower half of the mold, as seen in FIG. 9. In Example 2, a heat insulating member made from soft polyvinyl chloride and having the same thickness as that in Example 1 was applied to the lower half of the mold, and another heat insulating member of 3.0 mm thickness to the area near the bottom, as shown in FIG. 10. In Example 3, a heat insulating member of the same thickness as that in Example 1 made from soft polyvinyl chloride was attached at the narrower sides of the mold, as shown in FIG. 12. In each Example, subsequently, polyvinyl chloride plastisol composed of polyvinyl chloride (ZEON 131A), 100 parts by weight and DOP, 80 parts by weight was poured through a blood introducing tube to the level where it is brought in contact with the cover, as shown in FIG. 8B. The mold was dipped in a heating bath of 130° C. for 2 minutes, and then the plastisol was discharged in the way shown in FIG. 8D. The discharge technique permitted the production of tapered zone without steps at the boundary area between the portion of the heat insulating member attached to the mold or the outer member and the otherwise portion because plastisol flows down of itself. After terminating discharge, the heat insulating members were removed, and the metal mold was heated at 190° C. for 20 minutes. Then, after being allowed to cool to room temperature, the mold was removed. Thus the seamless unit of the cover and the blood chamber formed in a body were obtained.

Furthermore, the thickness of the portions of the molded blood chamber to which any insulating member have not been applied, except for the tapered zone along the boundary, was 1.7 mm alike in Examples 1, 2 and 3. The thickness of the thinnest zone to which the heat insulating member has been applied were 1.2 mm in Example 1, 1.2 mm in Example 2, and the thickness of the zone around the bottom to which a double heat insulating members have been applied doubly being 0.8 mm, and 1.3 mm in Example 3. By the way, the largest width D of the blood chamber indicated in FIG. 2 was 6.0 mm, the largest thickness W was 25 mm, and accordingly D/W is 2.4. The overall height L of the blood chamber along the center line indicated in FIG. 2 was 60 mm and D/L was 1.0.

As a comparative Example, a unit consisting of the cover and a blood chamber having no portion molded to relative smaller thickness was formed integrally and seamlessly in the same way as in Examples 1 to 3 except for application of heat insulating members.

The blood chamber-cover units obtained in Examples 1 to 3 and the Comparative Example each were placed in a housing 1 with the cover tightly attached. Then the inlet and outlet conduits for the blood 3 and 4 each were installed with a valve 6 or 7. Thus, blood pumps have been assembled. With each blood pump, heart assisting experiments through a left heart (ventricular) bypass were made at a stroke volume of the blood pumped out of 1.5 l/min over 44 days in a sheep. The blood chambers involved in Examples have proved to form no thrombus. The stroke volumes of the used blood pumps were all 50 ml. For comparison, a similar experiment was carried out with the blood pump free of appeared one of thickness according to the invention. It was necessary for the stroke volume to be at least 3.5 l/min for avoiding formation of thrombus over 30 days. At lower stroke volumes such as 1.5 l/ml which is the same as in Examples, thrombus was produced at the bottom of the sac-type blood chamber as the result of 7 days' beating. Besides, the stroke volume of the used blood pump was likewise 50 ml.

One of the advantages of the present invention resides in enabling it to form the portion near the bottom of the blood chamber to a smaller thickness than that of the other portions of that when compression accompanied, by reduction in volume of the blood chamber, beings, the reduction or deformation occurs initially at the zone defined by the opposite wider sides to bring them into contact with each other, directly followed by contact at the area near the bottom.

Another advantage of the present invention is to make it possible that the blood chamber has the opposite narrower side portions with smaller thickness than that of the remaining so that upon compression of the blood chamber accompanied by reduction in volume beings, the reduction occurs initially at the area near the bottom, and with increasing reduction of volume, the opposite wider sides are without fail flattened to close contact between them.

For the present invention may be used, as a matter of course, not only aqueous plastisol but also organosol of which the dispersion medium is an organic solvent.

The present invention enables on the basis of novel conception to mold an ideally-tapered thickness of blood chamber as desired. This improves artificial heart to be free of stagnation of the blood-stream which is great difficulty against putting into practical use of it, thus well contributing with great significance to the prevention against production of thrombus.

What is claimed is:

1. A method of making a blood pump having a blood chamber surrounded by a tapered wall, said wall therefore being of nonuniform thickness, comprising the steps of:
    putting a cover onto a cuplike mold in a liquid-tight manner, said cover being provided with an inlet conduit portion for introducing blood and an outlet portion for pumping out of the blood;
    covering at least a part of the outer surface of said mold with a non-metallic heat insulating material to control heat conduction through said part of the outer surface of said mold;
    pouring a plastisol of polyvinyl chloride into said mold to the level that said plastisol comes into contact with said cover;
    heating said mold from the exterior thereof so that a portion of said plastisol is gelled;
    discharging ungelled plastisol;
    removing said heat insulating material; and curing said gelled plastisol by reheating said mold from the exterior thereof.

2. A method according to claim 1, wherein the lower substantially-half portion of said mold is covered with a heat insulating material.

3. A method according to claim 1, wherein the portions of said mold corresponding to the narrower side and bottom areas of the blood chamber are covered with a heat insulating material.

4. A method according to claim 1, wherein the area near the bottom of said mold is covered at least doubly with heat insulating material.

5. A method according to claim 1, wherein the thickness of the portion of said blood chamber adjacent to said heat insulating material is molded to a thickness of 0.3 mm to 1 mm, and the thickness of the remaining portion is 1 to 3 mm.

6. A method according to claim 1, wherein the plastisol to be molded into a blood chamber is composed of 60 to 90 parts of dioctyl phthalate per 100 parts of polyvinyl chloride.

7. A method according to claim 1, wherein said plastisol is gelled at a temperature between 80° C. and 180° C.

8. A method according to claim 1, wherein, curing is performed at a temperature between 160° and 240° C.

9. A method according to claim 9, wherein curing is performed at a temperature between 190° C. and 210° C.

10. A method according to claim 1, wherein the inner surface of said blood pump is coated with an antithrombotic material.

11. A method according to claim 1, wherein said blood pump is oval in plan view and the ratio D/W, wherein D is the largest width of the broader side and W is the largest width of the narrower side in the unloaded state, is within the range of 1.5 to 3.0.

12. A method according to claim 1, wherein the ratio D/L, wherein D is the largest width of the broader side and L is the overall height of said blood chamber along the center line from the bottom to the largest width W, is $0.8 \leq D/L \leq 2.0$.

13. A method according to claim 1, wherein said nonmetallic heat insulating material is selected from the group consisting of polyvinyl chloride, polyvinyidene chloride, polyethylene terephthalate, nylon 6, nylon 66, polycarbonate, polysulfone, acryl resins, polyacetal resin, ABS resin, ebonite, polyurethane, epoxy resin, calcined carbon, ceramics, wood, asbestos, and cement.

* * * * *